United States Patent
Drasler et al.

(10) Patent No.: US 7,848,823 B2
(45) Date of Patent: Dec. 7, 2010

(54) CARDIAC STIMULATION SYSTEM

(75) Inventors: William J. Drasler, Minnetonka, MN (US); Michael J. Pikus, Golden Valley, MN (US); Roger Hastings, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 310 days.

(21) Appl. No.: 11/511,152

(22) Filed: Aug. 28, 2006

(65) Prior Publication Data

US 2007/0135882 A1    Jun. 14, 2007

Related U.S. Application Data

(60) Provisional application No. 60/748,964, filed on Dec. 9, 2005.

(51) Int. Cl.
*A61N 1/05* (2006.01)

(52) U.S. Cl. .......................... 607/126; 607/32

(58) Field of Classification Search .................. 607/126
See application file for complete search history.

(56) References Cited

U.S. PATENT DOCUMENTS

| | | | |
|---|---|---|---|
| 3,057,356 A | 9/1962 | Greatbatch | |
| 3,357,434 A | 12/1967 | Abell | |
| 3,596,662 A | 8/1971 | Bolduc | |
| 3,667,477 A | 6/1972 | Susset et al. | |
| 3,713,449 A | 1/1973 | Mulier | |
| 3,727,616 A | 4/1973 | Lenzkes | |
| 3,902,501 A | 9/1975 | Citron et al. | |
| 3,943,936 A * | 3/1976 | Rasor et al. | 607/35 |
| 4,010,756 A | 3/1977 | DuMont et al. | |
| 4,157,720 A | 6/1979 | Greatbatch | |
| 4,162,679 A | 7/1979 | Reenstierna | |
| 4,198,991 A | 4/1980 | Harris | |
| 4,256,115 A | 3/1981 | Bilitch | |
| 4,441,210 A | 4/1984 | Hochmair et al. | |
| 4,524,774 A | 6/1985 | Hildebrandt | |

(Continued)

FOREIGN PATENT DOCUMENTS

EP     0758542 A1    2/1997

(Continued)

OTHER PUBLICATIONS

"Energy management, wireless and system solutions for highly integrated implantable devices" Doctoral Thesis by Jordi Parramon I Piella for the Universitat Autonoma de Barcelona, certified Dec. 2001.

(Continued)

*Primary Examiner*—Carl H Layno
*Assistant Examiner*—Jeremiah T Kimball
(74) *Attorney, Agent, or Firm*—Schwegman, Lundberg & Woessner, P.A.

(57) ABSTRACT

Some embodiments of pacing systems employ wireless electrode assemblies to provide pacing therapy. The wireless electrode assemblies may wirelessly receive energy via an inductive coupling so as to provide electrical stimulation to the surrounding heart tissue. In certain embodiments, the wireless electrode assembly may be pivotable so that the proximal end of the wireless electrode assembly may be shifted to a position against the heart wall after the distal end has been secured to the heart wall.

27 Claims, 7 Drawing Sheets

U.S. PATENT DOCUMENTS

| | | |
|---|---|---|
| 4,641,664 A | 2/1987 | Botvidsson |
| 4,721,118 A | 1/1988 | Harris |
| 4,830,006 A | 5/1989 | Haluska et al. |
| 4,953,564 A | 9/1990 | Berthelsen |
| 4,987,897 A | 1/1991 | Funke |
| 5,012,806 A | 5/1991 | De Bellis |
| 5,139,033 A | 8/1992 | Everett et al. |
| 5,143,090 A | 9/1992 | Dutcher et al. |
| 5,170,802 A | 12/1992 | Mehra |
| 5,178,149 A | 1/1993 | Imburgia et al. |
| 5,193,539 A | 3/1993 | Schulman et al. |
| 5,255,693 A | 10/1993 | Dutcher et al. |
| 5,300,107 A | 4/1994 | Stokes et al. |
| 5,324,316 A | 6/1994 | Schulman et al. |
| 5,324,325 A | 6/1994 | Moaddeb |
| 5,336,252 A | 8/1994 | Cohen |
| 5,342,408 A | 8/1994 | deCoriolis et al. |
| 5,383,915 A | 1/1995 | Adams |
| 5,383,924 A | 1/1995 | Brehier |
| 5,411,535 A * | 5/1995 | Fujii et al. ............ 607/32 |
| 5,411,537 A | 5/1995 | Munshi et al. |
| 5,447,533 A | 9/1995 | Vachon et al. |
| 5,531,780 A | 7/1996 | Vachon |
| 5,571,148 A | 11/1996 | Loeb et al. |
| 5,622,168 A | 4/1997 | Keusch |
| 5,755,764 A | 5/1998 | Schroeppel |
| 5,772,693 A | 6/1998 | Brownlee |
| 5,779,715 A | 7/1998 | Tu |
| 5,800,535 A | 9/1998 | Howard, III |
| 5,814,089 A | 9/1998 | Stokes et al. |
| 5,833,715 A | 11/1998 | Vachon et al. |
| 5,851,227 A | 12/1998 | Spehr |
| 5,871,532 A * | 2/1999 | Schroeppel ............ 607/128 |
| 5,876,431 A * | 3/1999 | Spehr et al. ............ 607/126 |
| 6,035,239 A | 3/2000 | Patag et al. |
| 6,123,724 A | 9/2000 | Denker |
| 6,132,456 A | 10/2000 | Sommer et al. |
| 6,141,588 A | 10/2000 | Cox et al. |
| 6,141,591 A | 10/2000 | Lenarz et al. |
| 6,200,303 B1 | 3/2001 | Verrior et al. |
| 6,223,079 B1 | 4/2001 | Bakels et al. |
| 6,266,567 B1 | 7/2001 | Ishikawa et al. |
| 6,363,938 B2 | 4/2002 | Saadat et al. |
| 6,370,434 B1 | 4/2002 | Zhang et al. |
| 6,381,495 B1 | 4/2002 | Jenkins |
| 6,385,472 B1 | 5/2002 | Hall et al. |
| 6,445,953 B1 | 9/2002 | Bulkes et al. |
| 6,456,256 B1 | 9/2002 | Amundson et al. |
| 6,510,345 B1 | 1/2003 | Van et al. |
| 6,556,874 B2 | 4/2003 | Audoglio |
| 6,574,510 B2 | 6/2003 | Von Arx et al. |
| 6,582,441 B1 | 6/2003 | He et al. |
| 6,589,230 B2 | 7/2003 | Gia et al. |
| 6,614,406 B2 | 9/2003 | Amundson et al. |
| 6,647,292 B1 | 11/2003 | Bardy et al. |
| 6,895,280 B2 | 5/2005 | Meadows et al. |
| 6,907,285 B2 | 6/2005 | Denker et al. |
| 6,917,833 B2 | 7/2005 | Denker et al. |
| 7,003,350 B2 | 2/2006 | Denker et al. |
| 7,209,783 B2 | 4/2007 | Fellows et al. |
| 7,231,260 B2 | 6/2007 | Wallace et al. |
| 7,410,497 B2 | 8/2008 | Hastings et al. |
| 7,532,932 B2 | 5/2009 | Denker et al. |
| 7,532,933 B2 | 5/2009 | Hastings et al. |
| 7,615,010 B1 | 11/2009 | Najafi et al. |
| 7,647,109 B2 | 1/2010 | Hastings et al. |
| 7,650,186 B2 | 1/2010 | Hastings et al. |
| 2001/0018547 A1 | 8/2001 | Mechlenburg et al. |
| 2002/0077556 A1 | 6/2002 | Schwartz |
| 2002/0077685 A1 | 6/2002 | Sundquist et al. |
| 2002/0123785 A1 | 9/2002 | Zhang et al. |
| 2002/0138009 A1 | 9/2002 | Brockway et al. |
| 2002/0183791 A1 | 12/2002 | Denker et al. |
| 2002/0198604 A1 | 12/2002 | Schulman et al. |
| 2003/0036773 A1 | 2/2003 | Whitehurst et al. |
| 2003/0050681 A1 | 3/2003 | Pianca et al. |
| 2003/0074041 A1 * | 4/2003 | Parry et al. ............ 607/130 |
| 2003/0088278 A1 | 5/2003 | Bardy |
| 2003/0109914 A1 | 6/2003 | Westlund et al. |
| 2003/0158584 A1 | 8/2003 | Cates et al. |
| 2003/0181958 A1 | 9/2003 | Dobak, III |
| 2003/0181959 A1 | 9/2003 | Dobak, III |
| 2004/0059392 A1 | 3/2004 | Parramon et al. |
| 2004/0087831 A1 | 5/2004 | Michels et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0172083 A1 | 9/2004 | Penner |
| 2004/0176822 A1 | 9/2004 | Thompson et al. |
| 2005/0021108 A1 | 1/2005 | Klosterman et al. |
| 2005/0043765 A1 | 2/2005 | Williams et al. |
| 2005/0057905 A1 | 3/2005 | He et al. |
| 2005/0131511 A1 | 6/2005 | Westlund |
| 2005/0182456 A1 | 8/2005 | Ziobro et al. |
| 2005/0182465 A1 | 8/2005 | Ness |
| 2005/0251240 A1 | 11/2005 | Doan |
| 2005/0261741 A1 | 11/2005 | Libbus et al. |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095089 A1 | 5/2006 | Soykan et al. |
| 2006/0136001 A1 | 6/2006 | Ortega et al. |
| 2006/0136004 A1 | 6/2006 | Cowan et al. |
| 2007/0106357 A1 | 5/2007 | Denker et al. |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0203556 A1 | 8/2007 | Rutten et al. |
| 2007/0219590 A1 | 9/2007 | Hastings et al. |
| 2007/0239248 A1 | 10/2007 | Hastings et al. |
| 2008/0021505 A1 | 1/2008 | Hastings et al. |
| 2008/0021532 A1 | 1/2008 | Kveen et al. |
| 2008/0119911 A1 | 5/2008 | Rosero |
| 2009/0018599 A1 | 1/2009 | Hastings et al. |
| 2009/0204170 A1 | 8/2009 | Hastings et al. |
| 2009/0234407 A1 | 9/2009 | Hastings et al. |

FOREIGN PATENT DOCUMENTS

| | | |
|---|---|---|
| EP | 1 166 820 | 1/2002 |
| EP | 1166820 A2 * | 1/2002 |
| EP | 1166832 A1 | 1/2002 |
| EP | 1809372 A1 | 7/2007 |
| EP | 1835962 A1 | 9/2007 |
| FR | 2559391 | 8/1985 |
| JP | 05-076501 | 3/1993 |
| NZ | 526115 | 10/2006 |
| NZ | 539770 | 10/2007 |
| NZ | 539771 | 10/2007 |
| WO | WO-98/26840 A1 | 6/1998 |
| WO | WO-99/06102 A1 | 2/1999 |
| WO | WO-01/00114 A1 | 1/2001 |
| WO | WO-03/053491 A2 | 7/2003 |
| WO | WO 03053491 A2 * | 7/2003 |
| WO | WO-03/076010 A1 | 9/2003 |
| WO | WO-2005/101660 A1 | 10/2005 |
| WO | WO-2006/045073 A1 | 4/2006 |
| WO | WO-2006/045074 A2 | 4/2006 |
| WO | WO 2006/045075 | 4/2006 |

| WO | WO-2007/067231 A1 | 6/2007 |
| WO | WO-2007/067253 A1 | 6/2007 |
| WO | WO-2007/115044 A2 | 10/2007 |
| WO | WO-2008/011626 A1 | 1/2008 |
| WO | WO-2008/034005 A2 | 3/2008 |
| WO | WO-2008/111998 A1 | 9/2008 |

OTHER PUBLICATIONS

"Breakthrough Products Could Put Lesser-Known Firms on the Map", by E. Swain, *MDEA 2004*, pp. 56-58, Apr. 2004.

"Novel Passive Implantable Atrial Defibrillator Using Transcutaneous Radiofrequency Energy Transmission Successfully Cardioverts Atrial Fibrillation" by Manoharan et al., for *Circulation*, pp. 1382-1388, Sep. 16, 2003.

Wagner, "Electrodes, Leads, and Biocompatibility," *Design of Cardiac Pacemakers,* 1993, Chapter 6, pp. 133-160 and TOC.

"U.S. Appl. No. 11/683,584, Non-Final Office Action mailed Apr. 1, 2009", 9 pgs.

"U.S. Appl. No. 11/683,584, Response filed Jul. 1, 2009 to Non Final Office Action mailed Apr. 1, 2009", 7 pgs.

"International Application Serial No. PCT/US2005/037978, International Search Report mailed Jun. 13, 2006", 5 pgs.

"International Application Serial No. PCT/US2005/037978, Written Opinion mailed Jun. 13, 2006", 12 pgs.

"International Application Serial No. PCT/US2009/000693, International Search Report mailed May 8, 2009", 5 pgs.

"International Application Serial No. PCT/US2009/000693, Written Opinion mailed May 8, 2009", 8 pgs.

"U.S. Appl. No. 10/971,550, Response filed Feb. 22, 2007 to Restriction Requirement mailed Jan. 22, 2007", 1 pg.

"U.S. Appl. No. 10/971,550, Restriction Requirement mailed Jan. 22, 2007", 22 pgs.

"U.S. Appl. No. 10/971,550, Notice of Allowance mailed Dec. 22, 2008", 4 pgs.

"U.S. Appl. No. 10/971,550, Non-Final Office Action mailed Mar. 19, 2007", 11 pgs.

"U.S. Appl. No. 10/971,550, Non-Final Office Action mailed Nov. 5, 2007", 19 pgs.

"U.S. Appl. No. 10/971,550, Response Filed Sep. 4, 2007 to Non-Final Office Action mailed Mar. 19, 2007", 15 pgs.

"U.S. Appl. No. 10/971,550, Response filed Mar. 25, 2008 to Non Final Office Action mailed Nov. 5, 2007", 17 pgs.

"U.S. Appl. No. 10/971,550, Notice of Allowance mailed Jul. 14, 2008", 4 pgs.

"U.S. Appl. No. 11/549,352, Final Office Action mailed Mar. 9, 2009", 10 pgs.

"U.S. Appl. No. 11/683,577, Non Final Office Action mailed Mar. 5, 2009", 12 pgs.

"U.S. Appl. No. 11/549,352, Final Office Action mailed Aug. 26, 2008", 13 pgs.

"European Application Serial No. 06790023.3, Office Action Mailed Mar. 4, 2009", 6 pgs.

"European Application Serial No. 06825988.6, Office Action mailed Mar. 4, 2009", 7 pgs.

"International Application Serial No. PCT/US2006/040291, International Search Report mailed Apr. 4, 2007", 5 pgs.

"International Application Serial No. PCT/US2006/040291, Written Opinion mailed Apr. 4, 2007", 9 pgs.

"International Application Serial No. PCT/US2007/078405, International Search Report mailed May 20, 2008", 5 pgs.

"International Application Serial No. PCT/US2007/078405, Written Opinion mailed May 20, 2008", 7 pgs.

"International Application Serial No. PCT/US2005/037979, International Search Report mailed Mar. 21, 2006", 4 pgs.

"International Application Serial No. PCT/US2005/037979, Written Opinion mailed Mar. 21, 2006", 8 pgs.

"International Application Serial No. PCT/US2007/074135, International Search Report mailed Nov. 6, 2007", 4 pgs.

"International Application Serial No. PCT/US2007/074135, Written Opinion mailed Nov. 6, 2007", 8 pgs.

"Telemetry Research Transcutaneous Energy Transfer (TET) Technology Summary", *Telemetry Research Ltd.,* www.telemetryresearch.com, (date unknown), 1 pg.

Busch, M., et al., "On the Heating of Inductively Coupled Resonators (Stents) During MRI Examinations", *Magnetic Resonance in Medicine,* 54, (2005), 775-785.

Si, P., et al., "A Frequency Control Method for Regulating Wireless Power to Implantable Devices", *IEEE Transactions on Biomedical Circuits and Systems,* 2(1), (2008), 22-29.

"U.S. Appl. No. 11/683,577 Final Office Action Mailed Nov. 9, 2009", 19 pgs.

"U.S. Appl. No. 10/971,550, Amendment Under 37 C.F.R. Sec. 1.312 filed Mar. 20, 2009", 6 pgs.

"U.S. Appl. No. 11/075,375, Response filed Jul. 16, 2009 to Final Office Action mailed Apr. 16, 2009", 13 pgs.

"U.S. Appl. No. 11/075,376, Notice of Allowance mailed Aug. 24, 2009", 6 pgs.

"U.S. Appl. No. 11/075,376, Response filed Jul. 8, 2009 to Final Office Action mailed Apr. 8, 2009", 11 pgs.

"U.S. Appl. No. 11/316,120, Response filed Jul. 17, 2009 to Non Final Office Action mailed Apr. 17, 2009", 13 pgs.

"U.S. Appl. No. 11/394,601, Non-Final Office Action mailed Sep. 2, 2009", 6 pgs.

"U.S. Appl. No. 11/490,576, Non-Final Office Action mailed Oct. 5, 2009", 8 pgs.

"U.S. Appl. No. 11/490,916, Response filed Sep. 3, 2009 to Non Final Office Action mailed May 5, 2009", 13 pgs.

"U.S. Appl. No. 11/683,577, Response filed Aug. 5, 2009 to Non Final Office Action mailed Mar. 5, 2009", 10 pgs.

"U.S. Appl. No. 11/745,070, Response filed Jul. 27, 2009 to Non Final Office Action mailed Apr. 27, 2009", 11 pgs.

"U.S. Appl. No. 11/745,105, Non-Final Office Action mailed Sep. 18, 2009", 9 pgs.

"U.S. Appl. No. 11/549,352, Appeal Brief filed Sep. 9, 2009", 37 pgs.

"European Application Serial No. 07759589.0, Response filed Jun. 5, 2009 to Office Action mailed Jan. 29, 2009", 6 pgs.

"European Application Serial No. 05815215.8, Communication mailed Dec. 18, 2009", 2 pgs.

"European Application Serial No. 05817448.3, Communication mailed Dec. 18, 2009", 2 pgs.

"European Application Serial No. 07759589.0, Office Action Mailed Feb. 18, 2010", 3 pgs.

"U.S. Appl. No. 11/316,120, Final Office Action mailed Nov. 12, 2009", 8 pgs.

"U.S. Appl. No. 11/316,120, Non-Final Office Action mailed May 27, 2010", 8 pgs.

"U.S. Appl. No. 11/316,120, Response filed Apr. 12, 2010 to Final Office Action mailed Nov. 12, 2009", 12 pgs.

"U.S. Appl. No. 11/394,601, Final Office Action mailed Mar. 22, 2010", 7 pgs.

"U.S. Appl. No. 11/394,601, Response filed Dec. 2, 2009 to Non Final Office Action mailed Sep. 2, 2009", 11 pgs.

"U.S. Appl. No. 11/490,576, Response filed Mar. 5, 2010 to Non Final Office Action mailed Oct. 5, 2009", 13 pgs.

"U.S. Appl. No. 11/490,916, Final Office Action mailed Dec. 17, 2009", 11 pgs.

"U.S. Appl. No. 11/490,916, Response filed Apr. 15, 2010 to Final Office Action Received Dec. 17, 2009", 12 Pgs.

"U.S. Appl. No. 11/683,577, Response filed May 7, 2010 to Final Office Action mailed Nov. 9, 2009", 14 Pgs.

"U.S. Appl. No. 11/683,584, Final Office Action mailed Jan. 29, 2010", 9 pgs.

"U.S. Appl. No. 11/745,070, Final Office Action mailed Dec. 11, 2009", 18 pgs.

"U.S. Appl. No. 11/745,105, Final Office Action mailed Mar. 30, 2010", 9 pgs.

"U.S. Appl. No. 11/745,105, Response filed Jan. 19, 2010 to Non Final Office Action mailed Sep. 18, 2009", 12 pgs.

"U.S. Appl. No. 11/745,105, Response filed Jun. 22, 2009 to Restriction Requirement mailed May 21, 2009", 6 pgs.

"U.S. Appl. No. 11/745,105, Restriction Requirement mailed May 21, 2009", 6 pgs.

"European Application Serial No. 05815206.7, Communication Dec. 18, 2009", 4 pgs.

\* cited by examiner

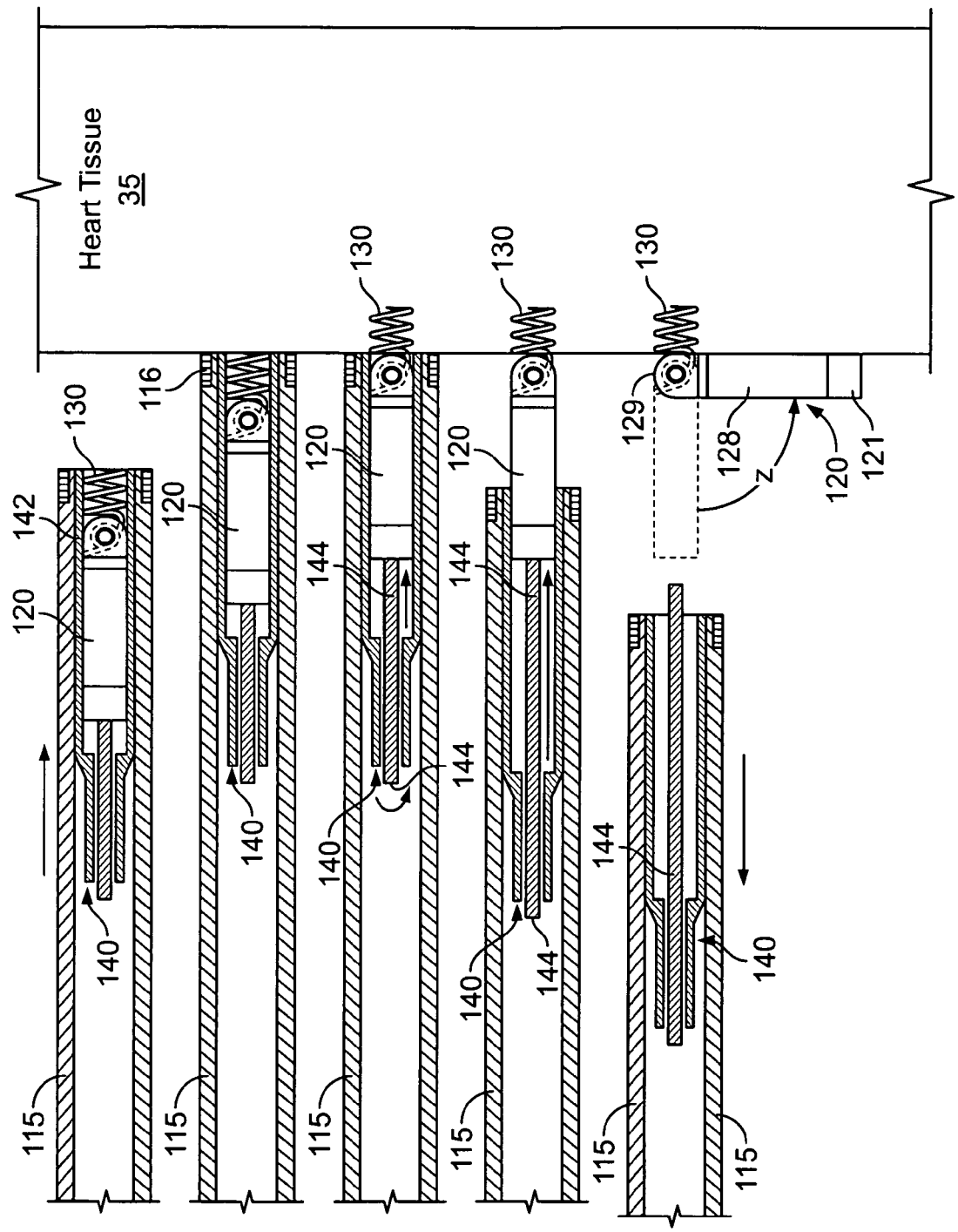

CARDIAC STIMULATION SYSTEM

CROSS REFERENCE TO RELATED APPLICATION

This application claims priority to U.S. Provisional Application Ser. No. 60/748,964 filed on Dec. 9, 2005 and entitled "CARDIAC STIMULATION SYSTEM," the contents of which are incorporated herein by reference.

TECHNICAL FIELD

This document relates to systems that electrically stimulate cardiac or other tissue.

BACKGROUND

Pacing instruments can be used to treat patients suffering from a heart condition, such as a reduced ability to deliver sufficient amounts of blood from the heart. For example, some heart conditions may cause or be caused by conduction defects in the heart. These conductions defects may lead to irregular or ineffective heart contractions. Some pacing instruments (e.g., a pacemaker) may be implanted in a patient's body so that pacing electrodes in contact with the heart tissue provide electrical stimulation to regulate electrical conduction in the heart tissue. Such regulated electrical stimulation may cause the heart to contract and hence pump blood.

Conventionally, pacemakers include a pulse generator that is implanted, typically in a patient's pectoral region just under the skin. One or more wired leads extend from the pulse generator so as to contact various portions of the heart. An electrode at a distal end of a lead may provide the electrical contact to the heart tissue for delivery of the electrical pulses generated by the pulse generator and delivered to the electrode through the lead.

The use of wired leads may limit the number of sites of heart tissue at which electrical energy may be delivered. For example, most commercially available pacing leads are not indicated for use in the left side of the heart. One reason is that the high pumping pressure on the left side of the heart may cause a thrombus or clot that forms on a bulky wired lead to eject into distal arteries, thereby causing stroke or other embolic injury. Thus, in order to pace the left side of the heart with a wired lead, most wired leads are directed through the cardiac venous system to a site (external to the left heart chambers) in a cardiac vein over the left side of the heart. While a single lead may occlude a cardiac vein over the left heart locally, this is overcome by the fact that other cardiac veins may compensate for the occlusion and deliver more blood to the heart. Nevertheless, multiple wired leads positioned in cardiac veins can cause significant occlusion, thereby limiting the number of heart tissue sites at which electrical energy may be delivered to the left side of the heart.

Some pacing systems may use wireless electrodes that are attached to the epicardial surface of the heart (external to the heart chambers) to stimulate heart tissue. In these systems, the wireless electrodes are screwed into the outside surface of the heart wall, which can reduce the effectiveness of the electrical stimulation in some circumstances.

SUMMARY

Some embodiments of pacing systems employ wireless electrode assemblies to provide pacing therapy. The wireless electrode assemblies may receive energy via an inductive coupling so as to provide electrical stimulation to the surrounding heart tissue. In certain embodiments, a wireless electrode assembly may be directed through a guide catheter in a heart chamber to deliver at least a portion of the wireless electrode assembly through the endocardium. For example, a distal end of the electrode assembly may include a helical tine so that the distal end may be secured into the inner wall of the heart chamber. In such circumstances, the electrode assembly may be pivotable so that the proximal end of the wireless electrode assembly may be shifted to a position against the heart wall after the distal end has been secured to the heart wall.

Some of the embodiments described herein may have one or more of the following advantages. First, the wireless electrode assemblies may eliminate or otherwise limit the need for wired pacing leads, thereby reducing the risk of stroke or other embolic injury from a thrombus or clot and reducing the risk of occluding cardiac veins (external to the heart chambers). Second, the wireless electrode assemblies may be secured to the inner wall of one more heart chambers, which may provide more efficient transfer of electrical stimulation. Third, the wireless electrode assemblies may be pivotable so that the proximal end shifts to a position against the heart wall after the distal end has been secured to the heart wall. In such circumstances, the contact of the wireless electrode assembly with the heart wall may increase the likelihood of incorporating the assembly into surrounding tissue, thereby further reducing the likelihood of forming a thrombus or clot in the heart chamber. Fourth, the pivoted electrode assembly may reduce the likelihood of the proximal end contacting and traumatizing the opposite chamber wall when the heart contracts (especially after the assembly has embedded into the surrounding tissue). Fifth, the pivoted electrode assembly may have a lower profile in the heart chamber to reduce the likelihood of interfering with a subsequent treatment catheter that is maneuvered in the same heart chamber. Sixth, when the wireless electrode assembly pivots to bring the proximal portion into contact with the heart chamber wall, there is a reduced likelihood of the dislodgement from the heart chamber wall.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 7A-E are a partial cross-sectional views of the wireless electrode assembly of FIG. 5 and an actuation rod, in accordance with some embodiments of the invention.

Like reference symbols in the various drawings indicate like elements.

DETAILED DESCRIPTION OF ILLUSTRATIVE EMBODIMENTS

Figure 1:
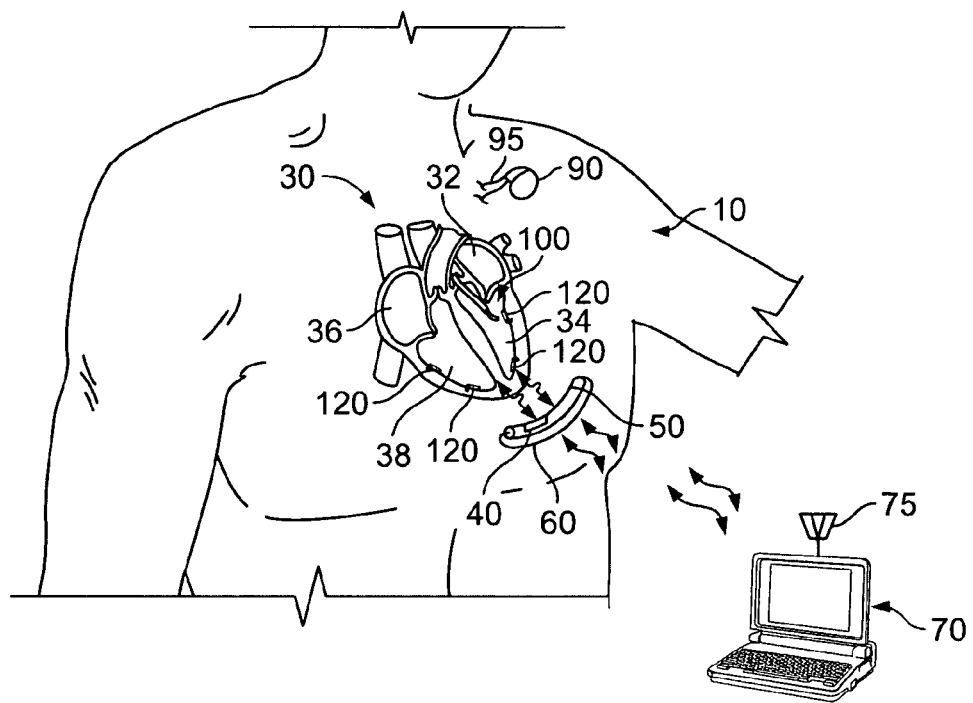
FIG. 1 is a perspective view of a stimulation system and at least a portion of an electrode delivery system, in accordance with some embodiments of the invention.

Referring to FIG. 1, an electrical stimulation system 10 may include one or more wireless electrode assemblies 120. The wireless electrode assemblies 120 are implanted within chambers of the heart 30. In this example, there are two implanted in the left ventricle 34 and two implanted in the right ventricle 38, but the wireless electrode assemblies may be implanted in the left atrium 32, the right atrium 36, or both. As described below in connection with FIGS. 4-9, the wireless electrode assemblies 120 may be delivered to one or more chambers of the heart 30 using an electrode delivery system 100. The electrode delivery system may include a guide catheter 110 that is directed through one or more veins or arteries to the targeted chamber of the heart 30 (e.g., the left ventricle 34 is the targeted chamber in the embodiment shown in FIG. 1). After the guide catheter 110 is deployed into the targeted heart chamber the wireless electrode assemblies 120 may be consecutively delivered through the guide catheter 110 using at least one delivery catheter 115, which may include a steering mechanism (e.g., steering wires, a shape memory device, or the like) to delivery the wireless electrode assembly 120 to the targeted site on the heart chamber wall.

The distal end of each wireless electrode assembly 120 may include a fixation device 130, such as a helical tine, to secure the wireless electrode assembly 130 to the heart chamber wall. After the fixation device 130 has secured an electrode assembly 120 to the heart chamber wall, the wireless electrode assembly may be pivotable so that the proximal end of the assembly 20 is shifted to a position against the heart chamber wall (described in more detail below in connection with FIGS. 4-9). In such circumstances, the pivotable electrode assembly 20 may increase the likelihood of incorporating the distal and proximal ends of the assembly into the adjacent heart tissue.

In some embodiments, each of the wireless electrode assemblies 120 may include a circuit comprising an internal coil and an electrical charge storage device (not shown in FIG. 1). As described in more detail below in connection with FIG. 3, the internal coil can be inductively coupled with an external power source coil so as to charge the electrical charge storage device (e.g., a battery, capacitor, or the like) contained within the wireless electrode assembly 120. Also in some embodiments, each of the wireless electrode assemblies 120 has a triggering mechanism in the circuit to deliver stored electrical charge to adjacent heart tissue (some examples are described in more detail below in connection with FIG. 3). In alternative embodiments, one or more of the wireless electrode assemblies 120 may have no energy storage device therein. In such circumstances, each wireless electrode assembly may be comprised, for example, of a ferrite core having caps at each end with ring electrodes encircling the caps. A number of turns of fine insulated wire may be wrapped around the central portion of the core so as to receive energy from a magnetic field produced by a shaped driving signal and designed to activate the electrodes.

Referring still to FIG. 1, the system 10 may also include a pacing controller 40 and a transmitter 50 that drives an antenna 60 for communication with the wireless electrode assemblies 120. The pacing controller 40 includes circuitry to sense and analyze the heart's electrical activity, and to determine if and when a pacing electrical pulse needs to be delivered and by which of the wireless electrode assemblies 120. The sensing capability may be made possible by having sense electrodes included within the physical assembly of the pacing controller 40. Alternatively, a conventional single or dual lead pacemaker may sense the local cardiac electrocardiogram (ECG) and transmit this information to antenna 60 for use by controller 40 in determination of the timing of wireless electrode assembly firing. In either case, the wireless electrode assembly 120 need not be provided with sensing capability, and also the wireless electrode assemblies 120 need not be equipped with the capability of communicating to the pacing controller 40 (for example, to communicate information about sensed electrical events). In alternative embodiments, the wireless electrode assemblies may communicate sensed information to each other and/or to the controller 40.

The transmitter 50—which is in communication with, and is controlled by, the pacing controller 40—may drive an RF signal onto the antenna 60. In one embodiment, the transmitter 50 provides both (1) a charging signal to charge the electrical charge storage devices contained within the wireless electrode assemblies 120 by inductive coupling, and (2) an information signal, such as a pacing trigger signal, that is communicated to a selected one or more of the wireless electrode assemblies 120, commanding that wireless electrode assembly 120 deliver its stored charge to the adjacent heart tissue.

One parameter of the wireless electrode assembly 120 that may affect the system design is the maximum energy required to pace the ventricle 34, 38 or other chamber of the heart 30. This energy requirement can include a typical value needed to pace ventricular myocardium, but also can include a margin to account for degradation of contact between the electrodes and tissue over time. In certain embodiments, each wireless electrode assembly 120 may require the maximum pacing threshold energy. This threshold energy is supplied to the wireless electrode assemblies between heartbeats by an external radio frequency generator (which may also be implanted), or other suitable energy source that may be implanted within the body. Parameter values for some embodiments may be:

Threshold pacing voltage=2.5 Volts
Typical lead impedance=600 Ohms
Typical pulse duration=0.4 mSec
Derived threshold energy=4 micro-Joules Because RF fields at frequencies higher than about 200 kHz may be attenuated by the body's electrical conductivity, and because electric fields of any frequency may be attenuated within the body, energy transmission through the body may be accomplished in some embodiments via a magnetic field at about 20-200 kHz (or by a magnetic field pulse that contains major frequency components in this range), and preferably by transmission of magnetic fields in the range of 100-200 kHz when transmission is through relatively conductive blood and heart muscle.

Still referring to FIG. 1, the pacing controller 40 and the transmitter 50 may be housed in a single enclosure that is implantable within a patient. In such a configuration, the single enclosure device may have a single energy source (battery) that may be either rechargeable or non-rechargeable. In another configuration, the pacing controller 40 and the transmitter 50 may be physically separate components. As an example of such a configuration, the pacing controller 50 may be implantable, for example in the conventional pacemaker configuration, whereas the transmitter 50 (along with the antenna 60) may be adapted to be worn externally, such as in a harness that is worn by the patient. In the latter example, the pacing controller 40 would have its own energy source (battery), and that energy would not be rechargeable given the relatively small energy requirements of the pacing controller 40 as compared to the energy requirements of the transmitter 50 to be able to electrically charge the wireless electrode assemblies 120. In this case, the pacing controller 40 would sense the local cardiac ECG signal through a conventional pacing lead, and transmit the sensed information to the external controller. Again, transmission of information, as opposed to pacing energy, has a relatively low power requirement, so a conventional pacemaker enclosure and battery would suffice.

The external programmer 70 is used to communicate with the pacing controller 40, including after the pacing controller 40 has been implanted. The external programmer 70 may be used to program such parameters as the timing of stimulation pulses in relation to certain sensed electrical activity of the heart, the energy level of stimulation pulses, the duration of stimulation pulse (that is, pulse width), etc. The programmer 70 includes an antenna 75 to communicate with the pacing controller 40, using, for example, RF signals. The implantable pacing controller 40 is accordingly equipped to communicate with the external programmer 70, using, for example, RF signals. The antenna 60 may be used to provide such communications, or alternatively, the pacing controller 40 may have an additional antenna (not shown in FIG. 1) for external communications with the programmer 70, and in an embodiment where the transmitter 50 and antenna 60 are housed separately from the controller 40, for communications with the transmitter 50.

Still referring to FIG. 1, at least a portion of the system 10 is shown as having been implanted in a patient, and in addition, the programmer 70 is also shown that is external to the patient. The controller 40 and transmitter 50 may be housed in a device that is shaped generally elongate and slightly curved so that it may be anchored between two ribs of the patient, or possibly around two or more ribs. In one example, the housing for the controller 40 and transmitter 50 is about 2 to 20 cm long and about 1 to 10 centimeters cm in diameter, may be about 5 to 10 cm long and about 3 to 6 cm in diameter. Such a shape of the housing for the controller 40 and transmitter 50, which allows the device to be anchored on the ribs, may provide an enclosure that is larger and heavier than conventional pacemakers, and may provide a larger battery having more stored energy. In addition, the controller 40 may comprise a defibrillator that discharges energy to the heart 30 through electrodes on the body of controller 40 when fibrillation is sensed. Other sizes and configurations may also be employed as is practical.

In some embodiments, the antenna 60 may be a loop antenna comprised of a long wire that is electrically connected across an electronic circuit contained within the controller/transmitter housing, which circuit delivers pulses of RF current to the antenna 60, generating a magnetic field in the space around the antenna 60 to charge the wireless electrode assemblies 120, as well as RF control magnetic field signals to command the wireless electrode assemblies 120 to discharge. In such embodiments, the antenna 60 may comprise a flexible conductive material so that it may be manipulated by a physician during implantation into a configuration that achieves improved inductive coupling between the antenna 60 and the coils within the implanted wireless electrode assemblies 120. In one example, the loop antenna 60 may be about 2 to 22 cm long, and about 1 to 11 cm wide, and may be about 5 to 11 cm long, and about 3 to 7 cm wide. Placement of the antenna 60 over the ribs may provide a relatively large antenna to be constructed that has improved efficiency in coupling RF energy to the pacing wireless electrode assemblies 120.

As shown in FIG. 1, some embodiments of the system 10 may also include a pulse generator device 90 (or pacemaker device) and associated wired leads 95 which extend from the pulse generator device 90 and into one or more chambers of the heart 30 (e.g., into the right atrium 36). For example, the system 10 may include wired leads 95 from the pulse generator device 90 that extend into the right atrium 36 and the right ventricle 38 while wireless electrode assemblies are disposed in the left atrium 32 and the left ventricle 34. The pulse generator device 90 may be used to sense the internal ECG, and may also communicate with the controller 40 and/or transmitter 50 as previously described.

As previously described, in some embodiments, each of the wireless electrode assemblies 120 includes a rechargeable battery or other charge storage device. This battery may provide power for delivering pacing energy to the tissue, and for operating communications, logic, and memory circuitry contained within the assembly. In some alternative embodiments, a transmitter and an antenna may be external to the patient (as opposed to the implantable transmitter 50 and antenna 60 depicted in FIG. 1), and may serve to recharge the batteries within the electrode assemblies. The recharge transmitter and antenna may be incorporated into furniture, incorporated into the patient's bed, or worn by the patient (e.g., in a vest-type garment). Daily recharging for predetermined to periods (e.g., about 30 minutes) may be required in some cases. In these circumstances, the wireless electrode assemblies 120 may be autonomous pacemaker-like devices, which can sense the local electrogram and only pace when the local tissue is not refractory. Such electrodes may communicate with the programming unit 70 to receive pacing instructions and transmit data stored in local memory. In these embodiments, each wireless electrode assembly 120 may also communicate with other implanted wireless electrode assemblies 120. For example, one electrode assembly 120 in the right atrium, may be designated as the "master," and all other implanted electrodes are "slaves," that pace with pre-programmed delays relative to the "master." As such, a master electrode in the right atrium may only sense the heart's sinus rhythm, and trigger pacing of the slaves with programmed delays.

Figure 2:
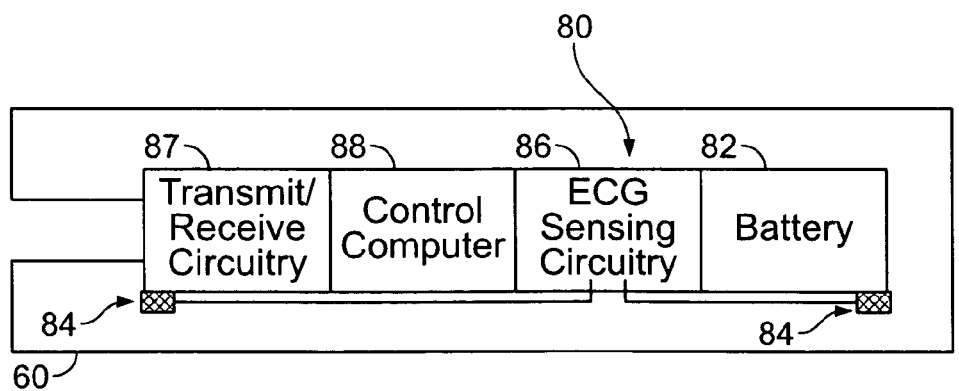
FIG. 2 is a diagram of at least a portion of a device of the stimulation system of FIG. 1.

Referring to FIG. 2, an embodiment of a device 80 including the controller 40, transmitter 50, associated antenna 60 is shown in block diagram form. Included within the device 80 is: a battery 82, which may be recharged by receiving RF energy from a source outside the body via antenna 60; ECG sensing electrodes 84 and associated sensing circuitry 86; circuitry 87 for transmitting firing commands to the implanted wireless electrode assemblies, transmitting status information to the external programmer, receiving control instructions from the external programmer and receiving power to recharge the battery; and a controller or computer 88 that is programmed to control the overall functioning of the pacing control implant. In alternative embodiments, antenna 60 may receive signals from the individual wireless electrode assemblies 120 containing information regarding the local ECG at the site of each wireless electrode assembly, and/or the antenna 60 may receive signals from a more conventional implanted pacemaker regarding the ECG signal at the sites of one or more conventional leads implanted on the right side of the heart.

Figure 3:
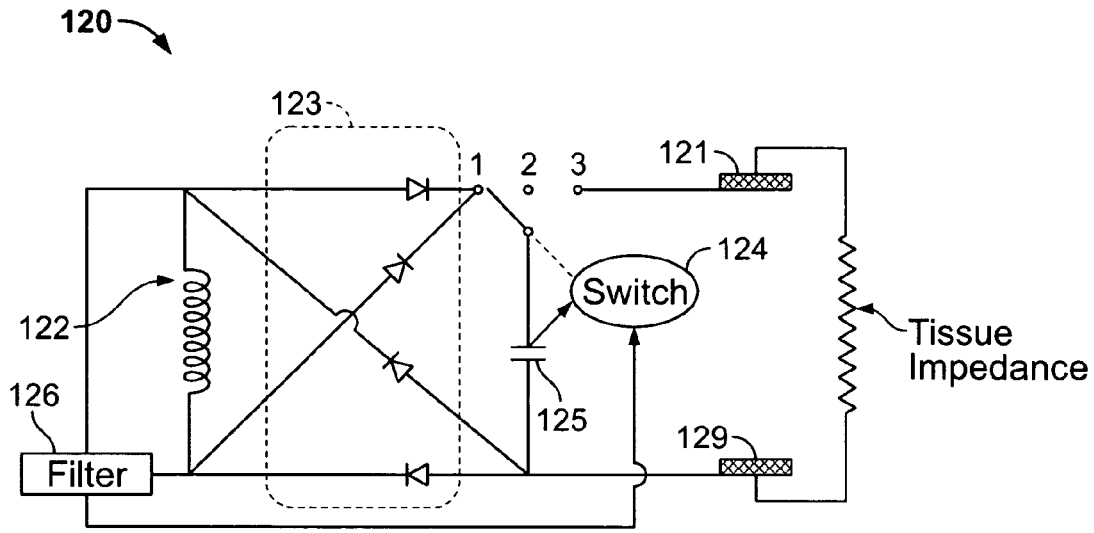
FIG. 3 is a diagram of at least a portion of a wireless electrode assembly of the stimulation system of FIG. 1.

Referring to FIG. 3, some embodiments of a wireless electrode assembly 120 may include a receiver coil 122 that is capable of being inductively coupled to a magnetic field source generating a time-varying magnetic field at the location of coil 122, such as would be generated by the transmitter 50 and the antenna 60 depicted in FIG. 1. The RF current in the external antenna may be a pulsed alternating current (AC) or a pulsed DC current, and thus the current induced through the receiver coil 122 would likewise be an AC or pulsed DC current. The current induced in coil 122 may be proportional to the time rate of change of the magnetic field generated at the site of coil 122 by the external RF current source. In some embodiments, a four-diode bridge rectifier 123 may connected across the receiver coil 122 to rectify the AC or pulsed DC current that is induced in the receiver coil 122. A three-position switch device 124 may be connected so that when the switch device 124 is in a first position, the rectifier 123 produces a rectified output that is imposed across a capacitor 125. As such, when the switch device 124 is in the position 1 (as is the case in FIG. 4), the capacitor 125 stores the induced electrical energy.

The switch device 124, in this example, is a voltage-controlled device and is connected to sense a voltage across the capacitor 125 to determine when the capacitor 125 has been sufficiently charged to a specified pacing threshold voltage level. When the capacitor 125 is sensed to have reached the specified pacing threshold level, the voltage-controlled switch device 124 moves to a position 2, which disconnects the capacitor 125 from the coil 122. With the switch device 124 in the position 2, the capacitor 125 is electrically isolated and remains charged, and thus is ready to be discharged. The voltage controlled switch device 124 may comprise a solid state switch, such as a field effect transistor, with its gate connected to the output of a voltage comparator that compares the voltage on capacitor 125 to a reference voltage. The reference voltage may be set at the factory, or adjusted remotely (e.g., after being implanted) via signals sent from the physician programmer unit 70 (FIG. 1), received by coil 122 and processed by circuitry not shown in FIG. 3. Any electronic circuitry contained within the wireless electrode assembly 120, including the voltage controlled switch, can be constructed with components that consume very little power, for example CMOS. Power for such circuitry is either taken from a micro-battery contained within the wireless electrode assembly, or supplied by draining a small amount of charge from capacitor 125.

Still referring to FIG. 3, a narrow band pass filter device 126 may also be connected across the receiver coil 122, as well as being connected to the three-position switch device 124. The band pass filter device 126 passes only a single frequency of communication signal that is induced in the coil 122. The single frequency of the communication signal that is passed by the filter device 126 may be unique for the particular wireless electrode assembly 120 as compared to other implanted wireless electrode assemblies. When the receiver coil 122 receives a short magnetic field burst at this particular frequency, the filter device 126 passes the voltage to the switch device 124, which in turn moves to a position 3.

With the switch device 124 in the position 3, the capacitor 125 may be connected in series through two bipolar electrodes 121 and 129, to the tissue to be stimulated. As such, at least some of the charge that is stored on the capacitor 125 is discharged through the tissue. When this happens, the tissue becomes electrically depolarized. In one example embodiment described in more detail below, the bipolar electrodes 121 and 129 across which stimulation pulses are provided are physically located at opposite ends (e.g., a proximal end and a distal end) of the wireless electrode assembly 120. After a predetermined, or programmed, period of time, the switch returns to position 1 so the capacitor 125 may be charged back up to the selected threshold level.

It should be noted that, for sake of clarity, the schematic diagram of FIG. 3 shows only the electrical components for energy storage and switching for particular embodiments of the wireless electrode assembly 120. Not necessarily shown are electronics to condition the pacing pulse delivered to the tissues, which circuitry should be understood from the description herein. Some aspects of the pulse, for example pulse width and amplitude, may be remotely programmable via encoded signals received through the filter device 126 of the wireless electrode assembly 120. In this regard, filter 126 may be a simple band pass filter with a frequency unique to a particular wireless electrode assembly, and the incoming signal may be modulated with programming information. Alternatively, filter 126 may consist of any type of demodulator or decoder that receives analog or digital information induced by the external source in coil 122. The received information may contain a code unique to each wireless electrode assembly to command discharge of capacitor 125, along with more elaborate instructions controlling discharge parameters such as threshold voltage for firing, duration and shape of the discharge pulse, etc.

Using wireless electrode assemblies of the type shown in FIG. 3, all of the implanted wireless electrode assemblies 120 may be charged simultaneously by a single burst of an RF charging field from a transmitter antenna 60. Because back reaction of the wireless electrode assemblies 120 on the antenna 60 may be small, transmitter 50 (FIG. 1) losses may be primarily due to Ohmic heating of the transmit antenna 60 during the transmit burst, Ohmic heating of the receive coil 122, and Ohmic heating of conductive body tissues by eddy currents induced in these tissues by the applied RF magnetic field. By way of comparison, if eight wireless electrode assemblies 120 are implanted and each is addressed independently for charging, the transmitter 50 may be turned ON eight times as long, which may require almost eight times more transmit energy, the additional energy being primarily lost in heating of the transmit antenna 60 and conductive body tissues. With the wireless electrode assembly 120 of FIG. 3, however, all implanted wireless electrode assemblies can be charged simultaneously with a burst of RF current in antenna 60, and antenna and body tissue heating occurs only during the time required for this single short burst. Each wireless electrode assembly is addressed independently through its filter device 126 to trigger pacing. The transmitted trigger fields can be of much smaller amplitude, and therefore lose much less energy to Ohmic heating, than the transmitted charging pulse.

Pending U.S. patent application Ser. Nos. 10/971,550 (filed on Oct. 20, 2004), 11/075,375 (filed on Mar. 7, 2005), and 11/075,376 (filed on Mar. 7, 2005), all owned by the assignee of this application, describe various features of wireless electrode assemblies, systems to deliver the wireless electrode assemblies to the heart, and electronic components to activate the wireless electrode assemblies to deliver electrical stimulation. It should be understood from the description herein that some of the features described in these three patent applications (Ser. Nos. 10/971,550, 11/075,375, and 11/075,376) may be applicable to particular embodiments described herein.

Figure 4:
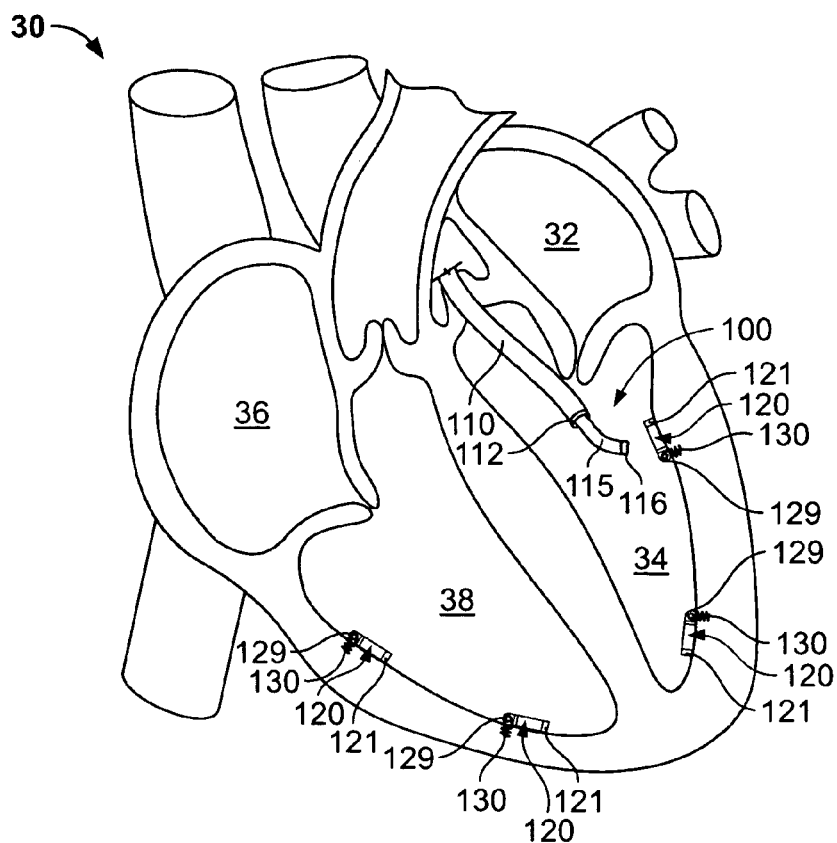
FIG. 4 is a section view of a heart and at least a portion of the electrode delivery system of FIG. 1.

Referring now to FIG. 4, some embodiments of an electrode delivery system 100 may include a guide catheter 110 and a delivery catheter 115. One or both of the catheters 110 and 115 may comprise an elongate body that extends from a proximal end (outside the patient's body, not shown in FIG. 4) to a distal end (depicted in FIG. 4 as extending into the patient's heart 30). The guide catheter 110 may be directed through one or more veins or arteries to the targeted chamber of the heart 30 (e.g., the left ventricle 34 is the targeted chamber in the embodiment shown in FIG. 4). The guide catheter 110 may comprise a steering mechanism (e.g., steering wires, shape memory device, or the like) to shift the distal end and may include at least one marker band 112 to permit viewability of the distal end of the guide catheter 110 using medical imaging techniques. Such a marker band 112 may aid a physician when steering the guide catheter 110 to the targeted heart chamber.

After the guide catheter 110 is deployed into the targeted heart chamber the wireless electrode assemblies 120 may be consecutively delivered through the guide catheter 110 using at least one delivery catheter 115. The delivery catheter 115 may include a steering mechanism (e.g., steering wires, shape memory device, or the like) to shift the distal end. For example, the delivery catheter may comprise a shape memory device (e.g., one or more wires comprising Nitinol or another shape memory material) to provide a predetermined curvature near the distal end of the delivery catheter. The shape memory device may be activated by a change in electrical charge or by a change in temperature. In one example, the delivery catheter 115 may include a shape memory device near the distal end that is capable of providing a 90-degree deflection curve near the distal end immediately before a longitudinally straight section at the distal end of the catheter 115. Also, in some embodiments, the delivery catheter 115 may include at least one marker band 116 to permit viewability of the distal end of the delivery catheter 115 using medical imaging techniques The delivery catheter 115 includes an opening at the distal end in which an associated wireless electrode assembly 120 is retained in a loaded position. The wireless electrode assembly 120 may include a body portion that has a length and a radius configured to be retained with the delivery catheter 115. As described in more detail below, some embodiments of the body portion of the wireless electrode assembly 120 may have a radius, for example, of about 1.25 mm or less and may have a length, for example, of about 10 mm or less. After the delivery catheter 115 is separated from the wireless electrode assembly 120, the wireless electrode assembly 120 may pivot to an deployed position so that proximal electrode 121 shifts toward the heart chamber wall (as described in more detail below, for example, in connection with FIGS. 6-9). In some embodiments, the opening at the distal end of the delivery catheter 115 may be part of conduit that extends through the elongated body of the catheter 115. In other embodiments, the opening at the distal end of the delivery catheter 115 may extend only a partial length into the delivery catheter 115 (e.g., with a narrower channel extending fully to the proximal end of the delivery catheter).

Figure 5:
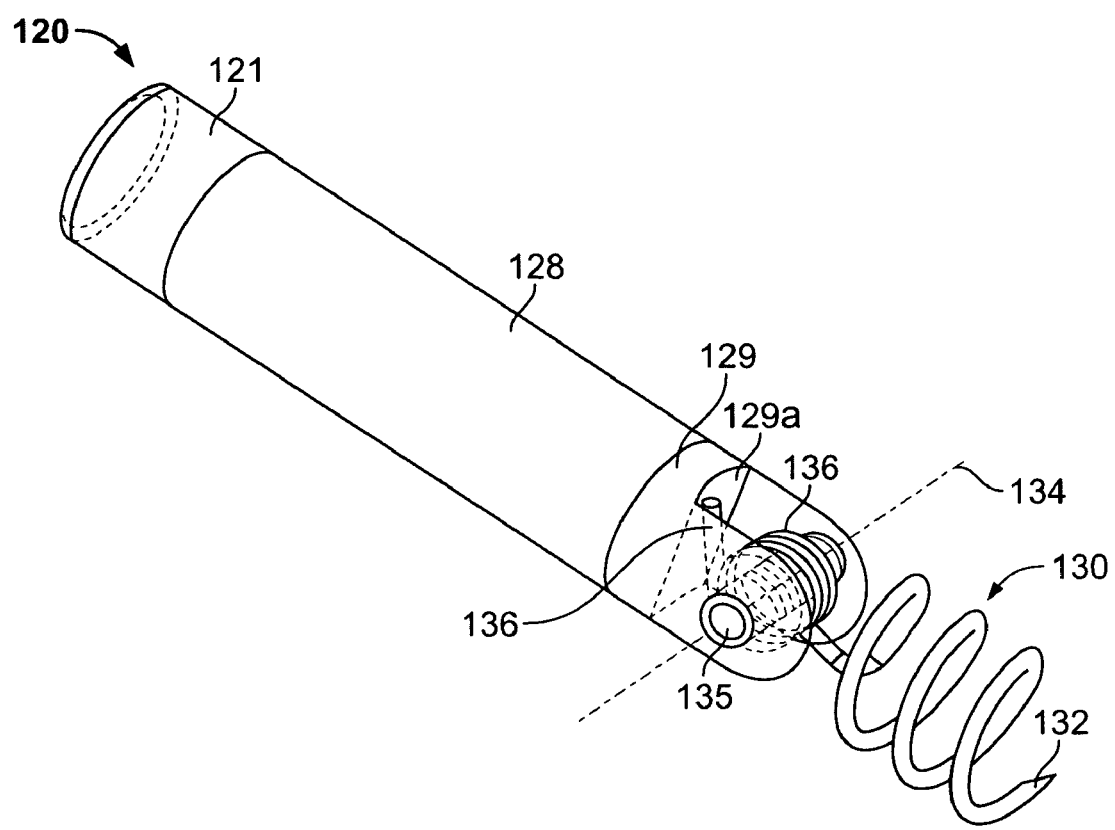
FIG. 5 is a perspective view of a wireless electrode assembly, in accordance with some embodiments of the invention.

Referring to FIG. 5, the wireless electrode assembly 120 may include a proximal electrode 121 at or near a proximal end and a distal electrode 129 at or near a distal end. The proximal electrode 121 and distal electrode 129 may provide bipolar electrode capabilities for the wireless electrode assembly 120, thereby permitting the assembly 120 to supply an electrical charge between the proximal and distal electrodes 121 and 129 (and across the nearby heart tissue). The distal end of the wireless electrode assembly 120 may also include a fixation device 130, such as a helical tine, to secure the wireless electrode assembly 120 to the heart chamber wall. For example, the distal tip 132 of the helical tine 130 may engage the heart chamber wall, and when a torque is applied to the wireless electrode assembly 120, the helical tine 130 may screw through the endocardium (e.g., the inner lining of the heart chamber wall) and possibly into the myocardium. Such a configuration permits the wireless electrode assembly 120 to be secured to the heart chamber wall.

At least a portion of the wireless electrode assembly 120 may be pivotable relative to a portion of the fixation device 130. In the embodiment depicted in FIG. 5, the body 128 of the wireless electrode assembly 120 is pivotable about a pin axis 134 relative to the fixation device 130. For example, the fixation device 130 may include a biasing portion 136 that is coiled around a pin 135 and presses against a portion of the electrode body 128 (e.g., presses against the end face 129a of distal electrode 129). As such, the biasing portion 136 applies a torque load so that the body 128 of the wireless electrode assembly 120 is pivotable about a pin axis 134 relative to the fixation device 130. As previously described, the wireless electrode assembly 120 may be arranged in the delivery catheter 115 (FIG. 4) so that the biasing portion 136 is in a loaded condition. In some embodiments, the biasing portion is in a loaded condition when the fixation device 130 extends in a generally longitudinal direction from the body 128 of the wireless electrode assembly 120 (refer, for example, to FIGS. 6A-B). Thus, when the delivery catheter 115 is retracted or otherwise separated from the wireless electrode assembly, the biasing portion 136 presses against the end face 129a of the body 128 so as to urge the body 128 to pivot about the pin axis 134.

Still referring to FIG. 5, in some embodiments of the wireless electrode assembly 120, the fixation device 130 may also serve as at least a portion of the distal electrode 129. For example, the fixation device 130 may comprise an electrically conductive material (e.g., a metallic material or the like) and may be electrically connected to the distal electrode circuitry so as to serve as at least a portion of the distal electrode. In the embodiment depicted in FIG. 5, a portion of the fixation device 130 is in contact with the end face 129a of the distal electrode 129, thereby causing the fixation device 130 to electrically stimulate the surround heart wall tissue (including the myocardium in some embodiments) when the wireless electrode assembly 120 is activated.

Figure 6A:
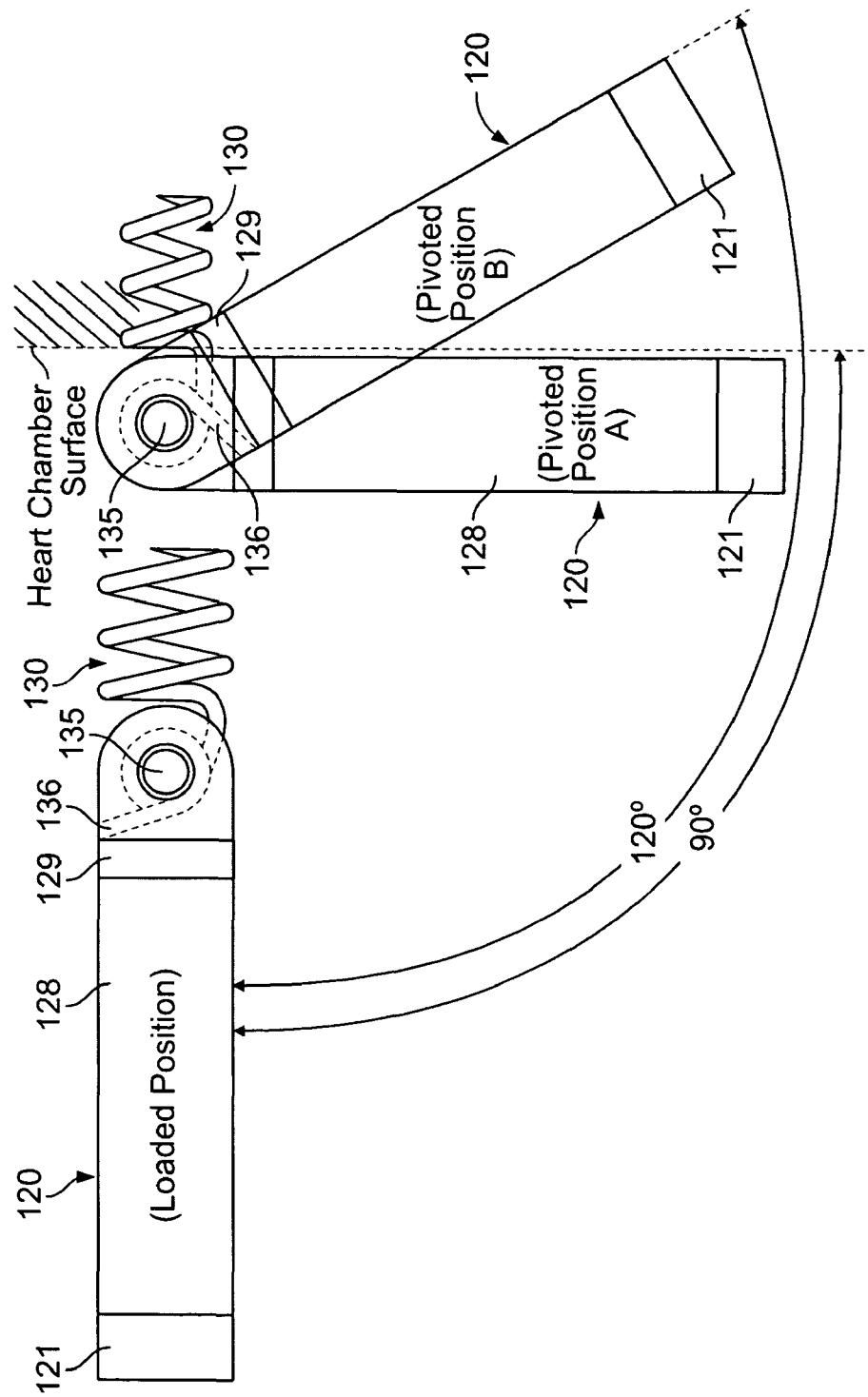
FIGS. 6A-B are views of the wireless electrode assembly of FIG. 5 arranged in different positions.
Figure 6B:
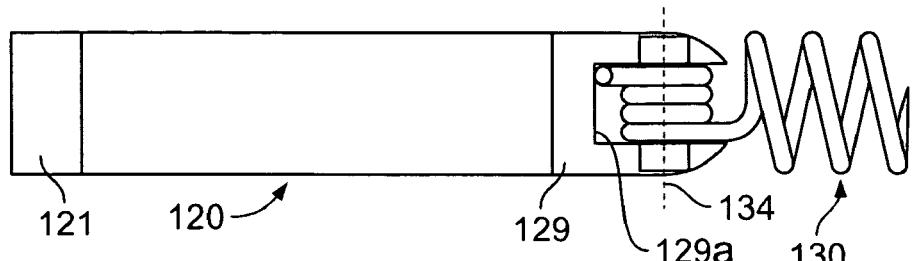

Referring to FIGS. 6A-B, the pivotable electrode assembly 120 may continue to be at least partially biased toward the heart chamber wall when the body 128 of the wireless electrode assembly is shifted to a position against the heart chamber wall. For example, the wireless electrode assembly 120 may be retained in the delivery catheter 115 (FIG. 4) in a loaded position, which in this embodiment allows the application of a twisting torque to the body 128 causes the fixation device 130 to be secured to the heart chamber wall. After the delivery catheter 115 is retracted or otherwise separated from the wireless electrode assembly 120, the body 128 is pivoted relative to the fixation device 130 so that the proximal electrode is shifted toward the heart chamber wall (refer to pivoted position A in FIG. 6A). In this pivoted position A, the biasing portion 136 may continue to apply a torque so that the body of the wireless electrode assembly 120 is retained against the heart chamber wall. As such, the biasing portion 136 is not necessarily completely unloaded when the body 128 of the wireless electrode assembly 120 is in the pivoted position A. Rather, in such embodiments, the spring force of the biasing portion 136 could be completely unloaded if the body 128 of the wireless electrode assembly 120 was permitted to pivot to a substantially greater angle (refer to pivoted position B in FIG. 6A).

Still referring to FIGS. 6A-B, the amount of torque applied by the biasing portion 136 when the body of the wireless electrode assembly 120 is retained against the heart chamber wall (refer to pivoted position A in FIG. 6A) may be affected by a number of factors. For example, if the torque provided by the biasing portion 136 in pivoted position A is too great, the body 128 of the wireless electrode assembly 120 could excessively dig into and traumatize the tissue of the heart chamber wall. Further, if the torque provided by the biasing portion 136 in pivoted position A is too great, such torque may cause an outward dislodging force on the fixation device 130. However, if the torque provided by the biasing portion 136 in pivoted position A is too small, the proximal end of the wireless electrode assembly 120 may shift or flop away from the heart chamber wall as the heart forcefully contracts during systole.

In some embodiments, the movement of the wireless electrode assembly 120 may be substantially reduced so that tissue may grow over and surround the wireless electrode assembly 120 in a period of days to weeks. In these embodiments, the wireless electrode assembly 120 may be immobilized by the surrounding tissue to prevent future dislodgement. In such circumstances, one may prescribe the patient to receive anti-coagulants, Aspirin, or other drugs (e.g., PLAVIX, CUMODIN, etc.) for several months after the operation or until incorporation of the wireless electrode assembly 120 into the surrounding tissue has occurred.

In some embodiments, the movement of the wireless electrode assembly 120 may be substantially reduced when the torque applied by the biasing portion 136 (in the pivoted position A) is at least equal to the opposing torque exerted on the body 128 of the wireless electrode assembly 120 by the contracting heart wall. In these circumstances, the force exerted at any point on the wireless electrode assembly 120 by the contracting heart may be approximately equal to blood pressure, P, times the vertical (or normal) component of an area element of the body 128. Then, the torque exerted at that point may be equal to the force times the distance, x, from the pivot axis 134 near the distal end of the wireless electrode assembly 120. For purposes of approximation, one may presume that the blood pressure, P, is uniform along the length of the body 128 and then integrate to find the average torque exerted by the heart wall on the wireless electrode assembly 120:

$$\tau = (2/\pi) \int dx \int R d\theta \int xP \cos(\theta)$$

where $\tau$=torque (in Nt–m) exerted by the heart wall at the pivot of the assembly
R=radius (in m) of the body of the wireless electrode assembly
L=length (in m) of the body of the wireless electrode assembly
P=average blood pressure in Nt/m$^2$ And, in this approximation, the torque, xPdA, at each area element dA=Rdθ dx may be averaged over the bottom surface of the body 128. After performing the integration, the torque may be given by:

$$\tau = (PRL^2)/\pi$$

In these circumstances, the approximate torque applied by the biasing portion 136 when the wireless electrode assembly 120 is in pivoted position A (refer to FIG. 6A) can be estimated to be about 50 gram–mm to about 125 gram–mm. In one example, one possible estimation of the torque may be found by taking an average blood pressure as P=100 mmHg=1.3×10$^4$ Nt/m$^2$ and representative values for the body 128 radius and length as R=1.25 mm=0.00125 m, and L=10 mm=0.01 m, and find:

$$\tau = 5.2 \times 10-4 Nt-m \approx 50 \text{ gram–mm}$$

Continuing this example, because the pressure is not constant during the cardiac cycle, and increases rapidly as systole begins, the torque applied by the biasing portion 136 should be larger than this value. If a margin of about 50% is used to prevent the wireless electrode assembly 120 from bouncing off the wall at beginning systole, the biasing portion 136 may be implemented to apply a torque of about 75 gram–mm when the wireless electrode assembly 120 is in pivoted position A (refer to FIG. 6). Employing other representative values or a different margin may indicate the use of a biasing portion 136 that provides a torque in the range 50 gram–mm to 125 gram–mm, possibly about 60 gram–mm to about 100 gram–mm or about 70 gram–mm to about 85 gram–mm.

In some embodiments, the fixation device 130, or at least the biasing portion 136, may comprise biocompatible torsion spring materials, such as stainless steel or MP35N. These materials can be wound into torsion springs of the type disclosed to provide a torque in the range 50 gram–mm to 125 gram–mm, as previously described.

In some embodiments the wireless electrode assembly 120 may be configured such that the torque provided by the biasing portion 136 reduces over time. For example, the torque provided by the biasing portion 136 may significantly reduce or completely drop after a after a time period (e.g., few days or weeks after the electrode assembly 120 has had a chance to incorporate with tissue and is effectively attached to the myocardial wall). To allow this biasing torque to reduce or drop to zero, some or all of the biasing portion 136 may comprise a biodegradable material (such materials suitable for use in a heart chamber are known to those having skill in the art) that can supply a torque for a desired period of time prior to degradation within the body. After the body 128 of the wireless electrode assembly 120 has been sufficiently incorporated into the surrounding tissue, the torque from the biasing member 136 might not be required.

In alternative embodiments, the biasing portion 136 may be configured to provide a low amount of torque but employs a ratcheting mechanism to fixedly hold the electrode assembly 120 into a pivoted position (e.g., refer to pivoted position A in FIG. 6A) with respect to the fixation device 130. Thus, the biasing portion 136 may supply a small amount of torque to shift the body 128 to a second position against the heart chamber wall, in which case the ratcheting mechanism would engage the biasing portion 136, the body 128, or another component of the wireless electrode assembly 120 so as to retain the body 128 in the second position. Such a ratcheting mechanism may prevent the electrode body 128 from flopping movement within the heart chamber prior to its incorporation within the heart chamber wall.

Figure 6C:
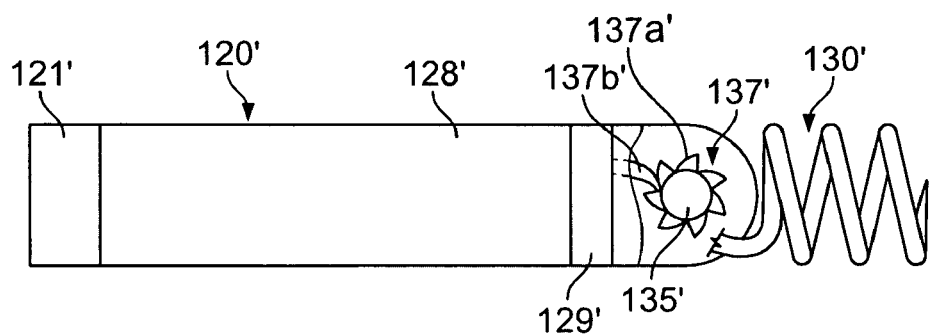
FIGS. 6C-D are views of a wireless electrode assembly in accordance with particular embodiments of the invention.

One illustrative example of such a ratcheting mechanism 137' is shown in FIG. 6C. In this example, the electrode assembly 120' has a body 128' that is pivotable relative to the fixation device 130' in a manner similar to previously described embodiments. The ratcheting mechanism 137' can include a ratchet wheel 137a' coupled with the fixation device 130' (e.g., disposed around the pin 135' with the biasing portion) and a pawl member 137b' coupled to the body 128'. As such, the ratcheting mechanism permits the body 128' to adjust in one direction to a pivoted position (refer, for example, to pivoted position A in FIG. 6A) with respect to the fixation device 130'. When the body 128' is in the pivoted position, the pawl member 137b' of the ratcheting mechanism 137') restricts the pivoting motion in the opposite direction, thereby retaining the body 128' against the heart tissue.

Figure 6D:
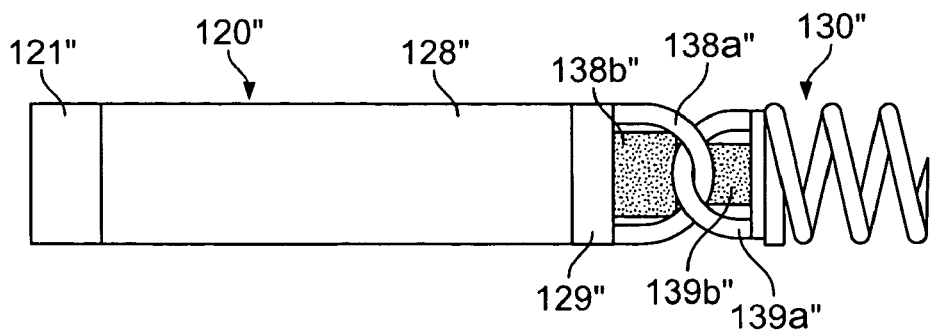

It should be understood from the description herein that the biasing portion of the electrode assembly is not limited to a coiled device. For example, as depicted in FIG. 6D, some embodiments of an electrode assembly 120" may include one or more viscous elements 138b" and 139b" that are capable of at least partially biasing the body 128" to remain in a particular orientation (e.g., proximate the heart chamber wall). In such embodiments, the viscous elements 138b" and 139b" may comprise a soft polymer material that exhibits viscoelasticity or may comprise another material that provides a dampening effect to resist movement of the body 128" relative to the fixation device 130". As shown in FIG. 6D, the body 128" can be coupled to the fixation device 130" in a manner that allows angulation of the body 128" relative to the fixation device 130". Here, the body 128" is coupled to the fixation device 130" using interlocking ring structures 138a" and 139a". As such, the body 128" is pivotable relative to the fixation device 130" to a desired angle in three dimensional space (e.g., movable in both the θ and φ directions in a spherical coordinate system). The viscous elements 138b" and 139b" can be disposed to engage the ring structures 138a" and 139a" so as to provide resistant to movement of the body 128" relative to the fixation device 130". Thus, after implantation of the fixation device 130", relative movement of the ring structures 138a" and 139a" permit motion of the body 128" so as to find an orientation (e.g., by environmental drift or by manual adjustment of the body 128" to overcome the viscoelastic resistance) that minimizes its movements. Thereafter, the viscous elements 138b" and 139b" can engage the ring structures 138a" and 139a" to dampen or further minimize the motion of the body portion 128" that would otherwise be compelled by the heart contractions. In these circumstances, the position of the wireless electrode assembly 120" can remain generally stable so as to increase the likelihood of incorporating the body 128" into the surrounding heart wall tissue.

Referring now to FIGS. 7A-E, some embodiments of the wireless electrode assemblies 120 may be press fit into the conduit of the delivery catheter 115 so that a plunger mechanism 144 may be used to separate the wireless electrode assembly 120 from the delivery catheter 115. As shown in FIG. 7A, the delivery catheter 115 may be steered and directed toward a targeted site at the surface of heart tissue 35 (e.g., a heart chamber wall). The wireless electrode assembly 120 may be releasably engaged with a tube portion 142 that is coupled to an actuation rod 140. In some embodiments, one or both of the actuation rod 140 and the plunger mechanism 144 may extend to an actuation device at the proximal end of the delivery catheter 115 outside the patient's body. For example, the wireless electrode assembly 120 may be press-fit into the tube portion 142 so that twisting the tube portion likewise causes the wireless electrode assembly 120 to twist. In another example, the tube portion 142 may be have a square cross-sectional shape, a hexagonal cross-sectional shape, a keyed cross-sectional shape, or other noncircular cross-sectional shape to engage the complementary shaped body 128 of the wireless electrode assembly 120. The tube portion 140 may be substantially rigid so as to retain the wireless electrode assembly 120 in a loaded condition (refer, for example, to FIGS. 5 and 6A-B).

As shown in FIG. 7B, the distal end of the delivery catheter 115 may abut the surface of the heart tissue 35 to prepare the wireless electrode assembly 120 for fixation to the tissue 35. In this embodiment, the distal end of the delivery catheter 115 includes a marker band 116 to facilitate the steering and guidance of the delivery catheter (e.g., a physician may employ medical imaging techniques to view the marker band 116 while the delivery catheter 115 is in the heart 30).

Referring to FIG. 7C, the actuation rod 140 may be twisted so as to engage the fixation device 130 with the tissue 35. In this embodiment, the fixation device 130 includes a helical tine that may be screwed into the tissue as the actuation rod 140 is twisted (which transfers a twisting torque from the tube portion 142 to the wireless electrode assembly 120). In some circumstances, a plunger mechanism 144 may force the wireless electrode assembly 120 toward the tissue 35 while the actuation rod 140 is twisted. Such an operation may drive the fixation device 130 into the tissue 35 as the helical tine is screwed further into the tissue 35.

Referring to FIG. 7D, after the fixation device 130 is secured to the tissue 35, the delivery catheter 115 (and the tube portion 142) may be separated from the wireless electrode assembly 120. This operation may be performed by forcing the plunger mechanism 144 against the proximal end of the wireless electrode assembly 120 to thereby retract the delivery catheter 115 away from the wireless electrode assembly 120.

Referring to FIG. 7E, when the delivery catheter is fully separated from the wireless electrode assembly 120, the biasing portion 136 of the wireless electrode assembly 120 may cause the body 128 to pivot so that the proximal end of the wireless electrode assembly 120 is shifted toward the surface of the tissue 35. As previously described, the biasing portion 136 of the wireless electrode assembly 120 may pivot to an angle of Z but may continue to bias the body 128 against the surface of the tissue so that the wireless electrode assembly 120 may be retained as such. In some embodiments, the tissue 35 may grow and eventually incorporate the wireless electrode assembly 120 therein, thereby preventing the wireless electrode assembly 120 from dislodgement from the tissue 35.

Figure 8:
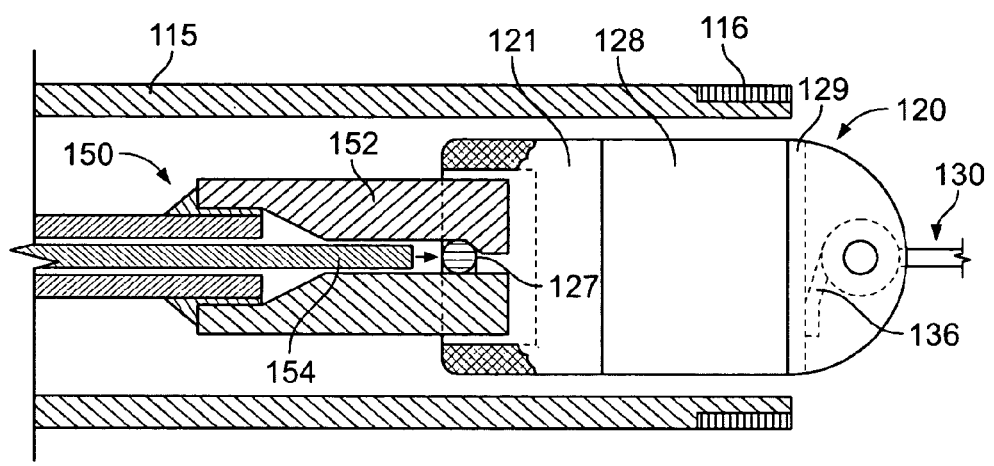
FIG. 8 is a partial cross-sectional view of the wireless electrode assembly of FIG. 5 and another actuation rod, in accordance with some embodiments of the invention.
Figure 9:
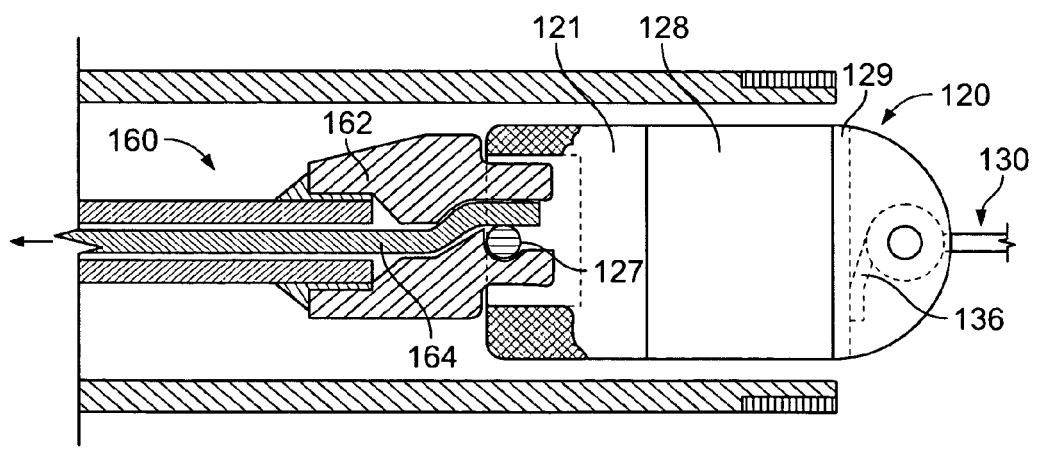
FIG. 9 is a partial cross-sectional view of the wireless electrode assembly of FIG. 5 and yet another actuation rod, in accordance with some embodiments of the invention.

Referring to FIGS. 8-9, other embodiments of an actuation rod may be employed to releasably retain the wireless electrode assembly 120. For example, referring to FIG. 8, an actuation rod 150 may include adaptor fingers 152 that retain the wireless electrode assembly 120 until a push mechanism 154 forces the wireless electrode assembly 120 to separate from the actuation rod 150 in the delivery catheter. The adaptor fingers 152 may grasp a retainer shaft 127 at the proximal end of the wireless electrode assembly 120. As such, the actuation rod 150 may be twisted, which causes a twisting torque to be transferred through the adaptor fingers 152 and to the wireless electrode assembly 120, thereby permitting the fixation device 130 to drive into the heart tissue (not shown in FIG. 8). After the fixation device 130 is secured into the heart tissue, a push mechanism 154 may press against the retainer shaft of the wireless electrode assembly 120 so that the adaptor fingers 152 retract away from the wireless electrode assembly 120. Then, the delivery catheter 115 and the actuation rod 150 may be separated from the wireless electrode assembly 120, and the biasing portion 136 may cause the body 128 to pivot toward the heart tissue, as previously described.

Referring to FIG. 9, another embodiment of an actuation rod 160 may include an adaptor 162 that engages the retainer shaft at the proximal end of the wireless electrode assembly 120. As such, the actuation rod 160 may be twisted, which causes a twisting torque to be transferred through the adaptor 162 and to the wireless electrode assembly 120, thereby permitting the fixation device 130 to drive into the heart tissue (not shown in FIG. 9). After the fixation device 130 is secured into the heart tissue, a pull wire 164 may be pulled away from the retainer shaft of the wireless electrode assembly 120 so that the adaptor fingers 162 becomes disengaged from the wireless electrode assembly 120. Then, the delivery catheter 115 and the actuation rod 160 may be separated from the wireless electrode assembly 120, and the biasing portion 136 may cause the body 128 to pivot toward the heart tissue, as previously described.

In some embodiments of the delivery catheter 115 described herein, the delivery catheter 115 may be wholly separate from the actuation rod 140, 150, 160, or 240 so that the actuation rod 140, 150, 160, or 240 slides through a conduit passing through the delivery catheter 115. In such circumstances, the actuation rod 140, 150, 160, or 240 may be completely retracted from the delivery catheter so that a second wireless electrode assembly may be detachably coupled to the actuation rod 140, 150, 160, or 240 (or to an unused, different actuation rod 140, 150, 160, or 240) and then directed through the delivery catheter 115 already disposed in the patient's body. In other embodiments, the delivery catheter 115 and the actuation rod 140, 150, 160, or 240 may be coupled to one another. In such circumstances, the delivery catheter 115 and actuation rod 140, 150, 160, or 240 may be removed from the guide catheter 110 (FIG. 4) so that a second wireless electrode assembly may be detachably coupled to the actuation rod 140, 150, 160, or 240 (or to a previously unused delivery catheter/actuation rod having a similar construction) and then directed through the guide catheter 110 already disposed in the patient's body.

Some of the embodiments described herein permit a plurality of pacing electrodes to be deployed at multiple pacing sites. The pacing sites may be located in the left atrium 32, the left ventricle 34, the right atrium 36, the right ventricle, or a combination thereof. Furthermore, the pacing electrodes may comprise wired pacing leads 95 (FIG. 1), wireless electrode assemblies, or a combination thereof. Providing electrical stimulation at multiple pacing sites and in multiple heart chambers may be used to treat a number of conditions. One such condition is congestive heart failure (CHF). It has been found that CHF patients have benefited from bi-ventricular pacing, that is, pacing of both the left ventricle 34 and the right ventricle 38 in a timed relationship. It is believed that many more patients could benefit if multiple sites in the left and right ventricles 34 and 36 could be synchronously paced. In addition, pacing at multiple sites may be beneficial where heart tissue through which electrical energy must propagate is scarred or dysfunctional, which condition halts or alters the propagation of an electrical signal through that heart tissue. In these cases multiple-site pacing may be useful to restart the propagation of the electrical signal immediately downstream of the dead or sick tissue area. Synchronized pacing at multiple sites on the heart may inhibit the onset of fibrillation resulting from slow or aberrant conduction, thus reducing the need for implanted or external cardiac defibrillators. Arrhythmias may result from slow conduction or enlargement of the heart chamber. In these diseases, a depolarization wave that has taken a long and/or slow path around a heart chamber may return to its starting point after that tissue has had time to re-polarize. In this way, a never ending "race-track" or "circus" wave may exist in one or more chambers that is not synchronized with normal sinus rhythm. Atrial fibrillation, a common and life threatening condition, may often be associated with such conduction abnormalities. Pacing at a sufficient number of sites in one or more heart chambers, for example in the atria, may force all tissue to depolarize in a synchronous manner to prevent the race-track and circus rhythms that lead to fibrillation.

A number of embodiments of the invention have been described. Nevertheless, it will be understood that various modifications may be made without departing from the spirit and scope of the invention. Accordingly, other embodiments are within the scope of the following claims.

What is claimed is:

1. A wireless electrode assembly for electrical stimulation of tissue in a heart chamber wall, comprising:
    a body portion that houses at least a portion of a circuit in electrical communication with at least one electrode to stimulate heart tissue;
    a fixation device configured to secure the body portion to an inner wall of a heart chamber;
    wherein at least a portion of the body portion is pivotable relative to at least a portion of the fixation device;
    wherein the body portion is sized and shaped for intravascular delivery to the inner wall of the heart chamber; and
    wherein the wireless electrode assembly includes a bias member configured to pivotally self-bias the body portion from a first position to a pivoted position relative to the fixation device.

2. The wireless electrode assembly of claim 1, wherein the body portion is pivotable relative to the fixation device from a first position to a pivoted position so that the body portion is operable to abut the inner wall surface of a heart chamber.

3. The wireless electrode assembly of claim 1, wherein the bias member applies a torque to the body portion when in the pivoted positioned of about 50 gram-mm to about 125 gram-mm.

4. The wireless electrode assembly of claim 1, wherein the bias member is integral with the fixation device.

5. The wireless electrode assembly of claim 4, wherein the fixation device and the bias member comprise stainless steel or MP35N material.

6. The wireless electrode assembly of claim 1, wherein the bias member comprises a viscoelastic material.

7. The wireless electrode assembly of claim 1, wherein the circuit comprises an internal coil to inductively couple with an external power source coil.

8. The wireless electrode assembly of claim 7, wherein the circuit comprises an electrical charge storage device that is recharged from current inductively generated by the internal coil.

9. The wireless electrode assembly of claim 1, wherein the fixation device is a tine that is insertable through endocardium and into myocardium of the heart chamber wall.

10. The wireless electrode assembly of claim 1, wherein the body portion includes a first electrode configured to contact heart tissue and configured to stimulate heart tissue;
    wherein the fixation device includes a second electrode configured to contact heart tissue and configured to stimulate heart tissue; and
    wherein the circuit is configured to deliver an electrical stimulation to the inner wall of the heart chamber between the first and second electrodes.

11. An electrode delivery system for delivering a wireless electrode assembly into a heart chamber, the system comprising:
    a wireless electrode assembly sized and shaped for intravascular delivery, the wireless electrode assembly including a body portion and biasing portion configured to pivot the body portion from a first position to a second position; and
    a delivery catheter configured to direct the wireless electrode assembly intravascularly to a heart chamber and toward an inner wall of the heart chamber, the delivery catheter including an opening in a distal end such that, when the wireless electrode assembly is separated from the opening in the distal end of the catheter, the biasing portion pivotally self-biases the body portion from the first position to the second position.

12. The electrode delivery system of claim 11, further comprising a guide catheter to direct the distal end of the delivery catheter into the heart chamber.

13. The electrode delivery system of claim 11, further comprising an actuation member to releasably engage the wireless electrode assembly when inside the delivery catheter.

14. The electrode delivery system of claim 13, wherein the actuation member comprises a push rod device to separate the wireless electrode assembly from the opening in the distal end of the delivery catheter.

15. The electrode delivery system of claim 13, wherein the actuation member comprises a pull wire device to release the wireless electrode assembly from the delivery catheter.

16. The electrode delivery system of claim 11, wherein the wireless electrode assembly comprises a fixation device that is insertable through endocardium and into myocardium of the heart chamber wall.

17. The electrode delivery system of claim 16, wherein the body portion is pivotable from the first position to the second position relative to the fixation device so that the body portion abuts the endocardium.

18. The electrode delivery system of claim 11, wherein the wireless electrode assembly comprises an internal coil to inductively couple with an external power source coil.

19. The electrode delivery system of claim 18, wherein the wireless electrode assembly comprises an electrical charge storage device that is recharged from current inductively generated by the internal coil.

20. The electrode delivery system of claim 11, wherein the body portion includes a first electrode configured to contact heart tissue and configured to stimulate heart tissue;
   wherein the biasing portion includes a second electrode configured to contact heart tissue and configured to stimulate heart tissue; and
   wherein the wireless electrode assembly includes a circuit configured to deliver an electrical stimulation to the inner wall of the heart chamber between the first and second electrodes.

21. A method of inserting a wireless electrode assembly into a heart chamber wall, comprising:
   securing a fixation device of a wireless electrode assembly through a portion of endocardium and into an inner wall of a heart chamber, the fixation device being disposed at a distal end of the wireless electrode assembly, and the wireless electrode assembly sized and shaped for intravascular delivery; and
   causing a body portion of the wireless electrode assembly to pivot relative to the fixation device using a bias member configured to pivotally self-bias a proximal end of the body portion toward the inner wall of the heart chamber.

22. The method of claim 21, wherein the body portion of the wireless electrode assembly is at least partially incorporated into the endocardium of the heart chamber wall over a period of time.

23. The method of claim 21, further comprising delivering the wireless electrode assembly through a delivery catheter to a targeted heart chamber.

24. The method of claim 23, wherein the wireless electrode assembly is pivotally self-biased from a first position to a pivoted position relative to the fixation device when the wireless electrode assembly is separated from an opening in a distal end of the delivery catheter.

25. The method of claim 24, further comprising actuating an actuation member to separate the wireless electrode assembly from the opening in the distal end of the delivery catheter.

26. The method of claim 21, further comprising implanting an external power source coil proximal to the heart so that the external power source coil is arranged for inductive coupling with an internal coil of the wireless electrode assembly.

27. The method of claim 21, wherein the body portion includes a first electrode configured to contact heart tissue and configured to stimulate heart tissue;
   wherein the fixation device includes a second electrode configured to contact heart tissue and configured to stimulate heart tissue; and
   wherein the method includes delivering an electrical stimulation to the inner wall of the heart chamber between the first and second electrodes.

* * * * *